United States Patent
Mohajer

(10) Patent No.: US 9,109,995 B2
(45) Date of Patent: Aug. 18, 2015

(54) METHOD AND APPARATUS FOR DETERMINING THE WATER CONCENTRATION IN A FLUID MIXTURE

(71) Applicant: Kam Controls, Inc., Houston, TX (US)

(72) Inventor: Kam Mohajer, Edwards, CO (US)

(73) Assignee: KAM Controls, inc., Houston, TX (US)

( * ) Notice: Subject to any disclaimer, the term of this patent is extended or adjusted under 35 U.S.C. 154(b) by 294 days.

(21) Appl. No.: 13/652,644

(22) Filed: Oct. 16, 2012

(65) Prior Publication Data

US 2014/0102181 A1   Apr. 17, 2014

(51) Int. Cl.
- *G01N 30/95* (2006.01)
- *G01N 27/00* (2006.01)
- *G01N 33/28* (2006.01)

(52) U.S. Cl.
CPC ............ *G01N 27/00* (2013.01); *G01N 33/2847* (2013.01); *G01N 33/2852* (2013.01)

(58) Field of Classification Search
CPC ............ G01N 33/2852; G01N 27/221; G01N 33/2847; G01N 33/5438
USPC ........................................................ 73/61.61
See application file for complete search history.

(56) References Cited

U.S. PATENT DOCUMENTS

| | | |
|---|---|---|
| 3,688,188 A | 8/1972 | Bak et al. |
| 4,112,744 A | 9/1978 | Tassano |
| 4,266,188 A | 5/1981 | Thompson |
| 4,646,070 A | 2/1987 | Yasuhara et al. |
| 4,862,060 A | 8/1989 | Scott et al. |
| 4,996,490 A | 2/1991 | Scott et al. |
| 5,014,010 A | 5/1991 | Helms et al. |
| 5,025,222 A | 6/1991 | Scott et al. |
| 5,033,289 A | 7/1991 | Cox |
| 5,101,163 A | 3/1992 | Agar |
| 5,103,181 A | 4/1992 | Gaisford et al. |
| 5,132,903 A | 7/1992 | Sinclair |
| 5,272,444 A | 12/1993 | Cox |
| 5,400,651 A | 3/1995 | Welch |
| 5,503,004 A | 4/1996 | Agar |
| 5,596,150 A | 1/1997 | Arndt |
| 5,675,259 A | 10/1997 | Arndt et al. |
| 5,723,979 A | 3/1998 | Mohr |
| 5,898,308 A | 4/1999 | Champion |
| 5,966,017 A | 10/1999 | Scott et al. |

(Continued)

FOREIGN PATENT DOCUMENTS

| | | |
|---|---|---|
| EP | 1756597 A1 | 2/2007 |
| WO | WO 01/92861 A2 | 12/2001 |
| WO | WO 2005/109012 A1 | 11/2005 |

*Primary Examiner* — Hezron E Williams
*Assistant Examiner* — Rodney T Frank
(74) *Attorney, Agent, or Firm* — Elizabeth R. Hall

(57) ABSTRACT

A measurement device for measuring water concentration in an oil water mixture has a transmitter that is used to transmit a designated spectrum of microwave frequencies to a transmitting antenna and then through the oil water mixture. A separate receiving antenna is used to detect the amplitude of each frequency of the transmitted spectrum after it has interacted with the oil water mixture. The detected signal from each microwave frequency that has interacted with the fluid mixture is digitized and sent to a processing unit. The processing unit receives the digitized frequencies and identifies the microwave frequency having the lowest amplitude, or amplitudinal nadir. The microwave frequency having the lowest amplitude is then used to calculate the percentage of water in the oil water mixture.

20 Claims, 5 Drawing Sheets

(56) References Cited

U.S. PATENT DOCUMENTS

| | | |
|---|---|---|
| 6,144,211 A | 11/2000 | Mohr |
| 6,614,238 B1 | 9/2003 | Jean et al. |
| 6,826,964 B2 | 12/2004 | Nyfors |
| 6,867,603 B2 | 3/2005 | Nicholson et al. |
| 6,927,583 B2 | 8/2005 | Vanzuilen et al. |
| 7,135,870 B2 | 11/2006 | Mohajer et al. |
| 2004/0135585 A1 | 7/2004 | Nagy |
| 2005/0057267 A1 | 3/2005 | Nicholson et al. |

METHOD AND APPARATUS FOR DETERMINING THE WATER CONCENTRATION IN A FLUID MIXTURE

BACKGROUND OF THE INVENTION

1. Field of the Invention

The present invention relates in general to a method and apparatus for determining the concentration of water in an oil water fluid mixture. More particularly, the present invention relates to a method and apparatus for determining the concentration of water within an oil water mixture based on the identification of a specific frequency transmitted to the fluid mixture that results in the lowest frequency signal after reacting with the fluid mixture.

2. Description of the Related Art

Knowledge of accurate water content in a petroleum fluid mixture is important for oilfield reservoir management, royalty allocation, buying and selling, corrosion management, refining, chemical processing, and aviation safety.

Current oil water measurement devices typically measure the ratio of fluids in an oil water fluid sample using radio frequency (RE) or microwave energy to determine the capacitance or permittivity of a fluid sample consisting of oil and water. Because permittivity is the measurement of a fluid's ability to resist an electronic field, the power required to maintain a specific frequency within that fluid is a function of permittivity.

In one embodiment of the currently available microwave systems, the oil water measurement device is emerged in a fluid emulsion of oil and water. Within the oil water measurement device an oscillator is connected to a single antenna. The antenna transmits one or more specific frequencies to the fluid emulsion and receives the load change in the current consumption of the oscillator. The current consumption of the oscillator is dependent on the composition of the mixture since various components have different dielectric constants, which are proportionally related to the overall impedance of the mixture.

The complex permittivity of many materials changes with the frequency used for the permittivity measurement. Thus, as the oscillator frequency is changed, the complex permittivity also changes and the resulting system of mathematical equations used to describe and solve for the component concentrations become increasingly non-linear. If, however, the permittivity measurements can be made at accurate and repeatable frequencies, the fluid system components could be determined hour simple linear equations.

Some of the newer microwave apparatus use multiple oscillators or voltage-controlled-oscillators (VCOs) to measure water concentrations in oil water mixtures at one or more specific frequencies. As with any electronics, these oscillators are subject to drift due to the temperature of the ambient surroundings or from self-heating and aging of the components. It is difficult, or impossible, to separate drifts in the oscillator from actual impedance changes in the fluid medium and as explained previously, non-linear dielectric constants tend to magnify the measurement errors.

A few of the systems include a reference oscillator calibrated to provide a specific frequency for a known impedance, but the reference oscillator is subject to the same thermal and aging errors. In fact, component aging and thermal effects might have offsetting effects and move the reference frequency in the opposite direction from the measurement frequency. Thus, the reference and measurement oscillators require frequent calibration and recalibration.

The device described in U.S. Pat. No. 7,135,870 measures the power consumed by the crystal oscillating loop and uses that measurement to determine the permittivity of the fluid which is related to the water content in the fluid. Signals, such as radio frequency or microwave, are sequentially transmitted at multiple, known, constant frequencies to and reflected from both a reference sensor and a measurement sensor. Permittivities of the individual components are determined from these transmitted and reflected signals and information about the concentration of the components of the fluid mixture is calculated.

There is an existing need for a simple automated device for accurately measuring water content in petroleum fluids containing low concentrations of water.

SUMMARY OF THE INVENTION

A method and apparatus are disclosed for determining low concentrations of water in an oil water fluid mixture. A transmitter is used to transmit a designated spectrum of microwave frequencies to a transmitting antenna and then through the oil water mixture. A separate receiving antenna is used to detect the signal of each frequency of the transmitted spectrum after it has interacted with the oil water mixture. The detected signal from each microwave frequency that has interacted with the fluid mixture is digitized and sent to a processing unit. The processing unit receives the digitized signal of each of the microwave frequencies transmitted through the fluid mixture and identities the microwave frequency having the lowest signal amplitude, hereinafter referred to as the amplitudinal null or an amplitudinal nadir. The microwave frequency having the lowest signal amplitude is then used to calculate the percentage of water in the oil water mixture.

One embodiment of the present invention is a device for determining the concentration of fluid components within a fluid mixture comprising: a) a microprocessor; b) a transmitter in communication with the microprocessor, the transmitter having a phase locked loop and a voltage controlled oscillator, wherein the transmitter generates and transmits a range of microwave frequencies; c) a receiver in communication with the microprocessor; d) a reference oscillator in communication with the phase locked loop of the transmitter; and c) a sensor probe including: (i) a transmitting antenna in communication with the transmitter, wherein the transmitting antenna receives the range of microwave frequencies generated by the transmitter and transmits the range of microwave frequencies to a fluid mixture, (ii) a receiving antenna in communication with the receiver, the receiving antenna receives a signal tram each frequency in the range of microwave frequencies transmitted through the fluid mixture, and (iii) a probe body having a fluid opening for allowing the fluid mixture to flow through the probe body in communication with the transmitting, antenna and the receiving antenna; whereby the frequency signal of the range of microwave frequencies received from the fluid mixture by the receiving antenna is communicated to the microprocessor via the receiver and is used to calculate a percentage of water in the fluid mixture.

A second embodiment of the present invention is a method for detecting the percentage of water in a fluid mixture including the steps of: (a) positioning a sensor probe of a measurement device within a fluid mixture, wherein the measurement device includes: (i) a microprocessor, (ii) a transmitter having a phase locked loop and a voltage controlled oscillator, the transmitter in communication with the microprocessor, (iii) a receiver in communication with the microprocessor, (iv) a reference oscillator in communication with the phase locked loop, and (v) a sensor probe having a transmitting antenna in communication with the transmitter and a receiving antenna in communication with the receiver, and a probe body having a fluid opening for allowing the fluid mixture to flow through the probe body in communication with the transmitting antenna and the receiving antenna; (b) selecting a spectrum of microwave frequencies, wherein the spectrum includes a plurality of frequencies; (c) utilizing the phase locked loop and the reference oscillator to lock a request for each of the plurality of frequencies into the voltage controlled oscillator; (d) generating each of the locked frequencies; (e) transmitting, the generated frequencies to the fluid mixture via the transmitting antenna; (f) receiving a signal via the receiving antenna from each of the transmitted frequencies after each frequency has interacted with the fluid mixture; (g) identifying a specific frequency within the spectrum of frequencies having a lowest amplitude of the received frequency signals; and (h) computing a percentage of water in the fluid mixture based on the specific frequency of lowest amplitude.

The foregoing has outlined rather broadly several aspects of the present invention in order that the detailed description of the invention that follows ma be better understood. Additional features and advantages of the invention will be described hereinafter which form the subject of the claims of the invention. It should be appreciated by those skilled in the art that the conception and the specific embodiment disclosed might be readily utilized as a basis for modifying or redesigning the structures for carrying out the same purposes as the invention. It should be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DESCRIPTION OF THE PREFERRED EMBODIMENTS

Figure 1:
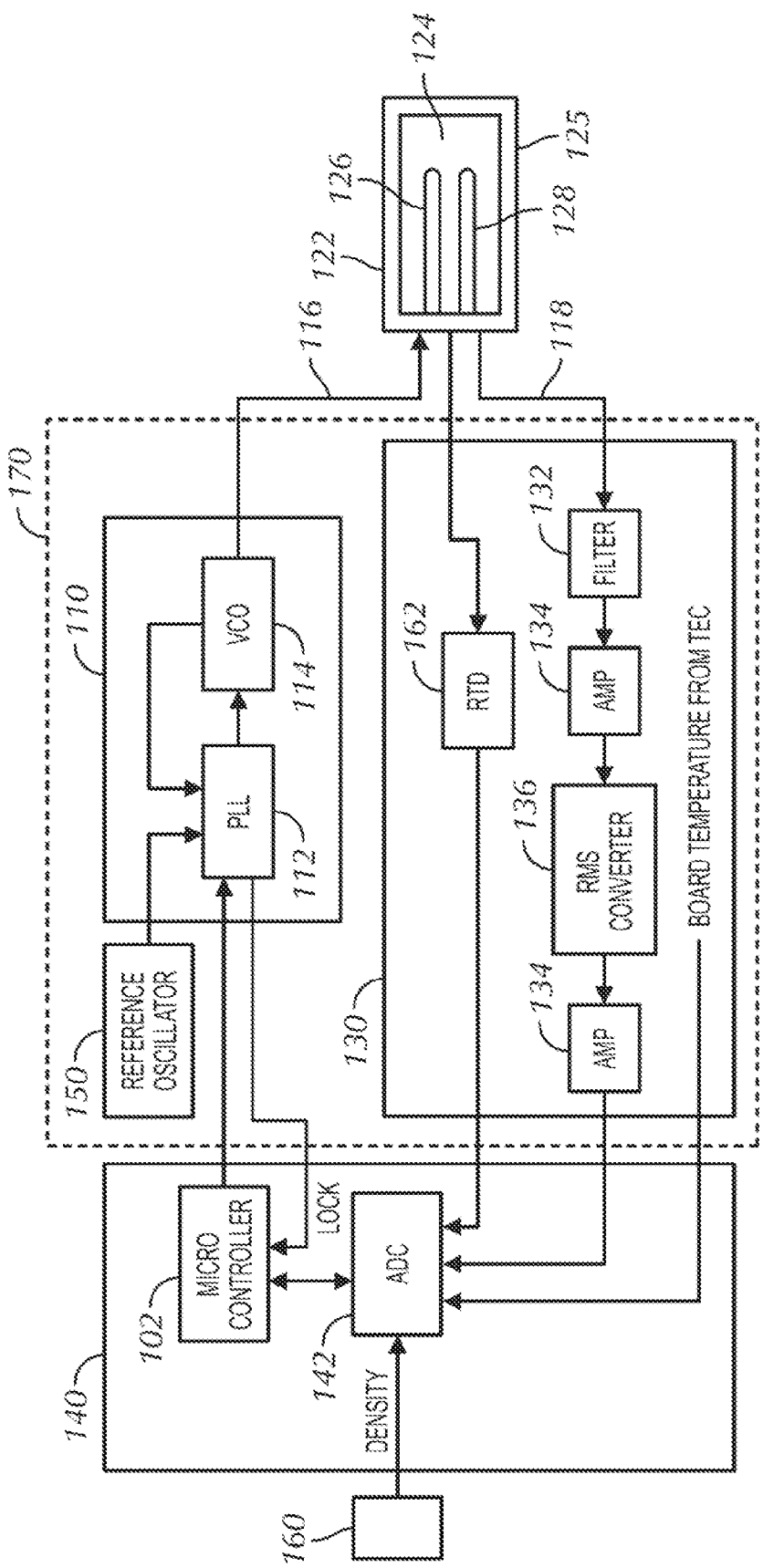
FIG. 1 is schematic representation of the measurement device.

The present invention includes a method and apparatus for accurately determining the concentration of components in a fluid mixture. In the discussion that follows, an oil water mixture or emulsion is used for illustrative purposes, but the fluid mixture is not limited to a mixture of water and petroleum or hydrocarbons. For example, embodiments of the present invention include a measurement device for measuring water concentration in an oil water mixture. Preferred embodiments accurately determine the water concentration in an oil water mixture when water makes up about 5% or less of the fluid mixture.

The measurement device has a transmitter that transmits a designated spectrum of microwave frequencies to a transmitting antenna and then through the oil water mixture. A separate receiving antenna detects each frequency signal of the transmitted frequency spectrum after it has interacted with the oil water mixture. The detected signal from each microwave frequency is digitized and sent to a processing unit. The processing unit receives the digitized signal of each of the microwave frequencies transmitted through the fluid mixture and identifies the microwave frequency having the lowest amplitude, or amplitudinal nadir, after interacting with the fluid mixture. The microwave frequency having the lowest amplitude is then used to calculate the percentage of water in the oil water mixture.

Several currently available oil water detectors utilize a one port system. A one port system utilizes an oscillator connected to an antenna that both transmits microwaves through the fluid mixture and receives the microwave signals transmitted through the fluid mixture. The one port oil water detectors typically determine the permittivity of the fluid mixture by measuring, the fluid's ability to resist an electronic field or the power required to maintain a specific frequency within the fluid mixture. Changes in the permittivity of the fluid mixture are used to calculate the composition of the oil water fluid mixture.

In contrast, embodiments of the present invention utilize a two port measurement system. In the two port measurement system an oscillator is connected to an antenna that transmits selected microwave frequencies through the fluid mixture. Then a second antenna, unconnected to the oscillator, receives the microwave signals after they pass through the fluid mixture. The electronic separation of the transmitting antenna and the receiving antenna allows the system to utilize a phase locked loop to confirm each frequency in the selected frequency spectrum that is transmitted. The ability to utilize the phase locked loop to confirm and lock each frequency in the transmitted frequency spectrum before it is transmitted essentially removes drift in the measurement device due to oscillator aging, or the effect of varying ambient temperatures on the device.

Referring now to the drawing's, it is pointed out that like reference characters designate like or similar parts throughout the drawings. The Figures, or drawings, are not intended to be to scale. For example, purely for the sake of greater clarity in the drawings, wall thickness and spacing are not dimensioned as they actually exist in the assembled embodiments.

A schematic of a first embodiment of the oil water measurement device 100 of the present invention is shown in FIG. 1. The measurement device 100 is configured for flange mounting on a fluid conduit (such as a pipeline 210 shown in FIG. 2). Typically, the probe 120 of the measurement device 100 is radially inserted into a flow stream 250 confined within a tubular conduit 210, such as a pipeline.

The flow conduit 210 is provided with a radial circular port either by having a welded mounting flange preinstalled with the port during fabrication or by being hot-tapped in service with a conventional hot-tap fitting and machine used to produce a port. Once the bead 125 of the sensor probe 120 has been installed in the pipeline 210 and its position adjusted appropriately, the lower tip of sensor head 125 is positioned so that the fluid flow 250 passes freely through the fluid opening 124 in the sensor probe 120 and the transmitting antenna 126 and the receiving antenna 128 are fully exposed to the fluid flow 250.

Figure 2:
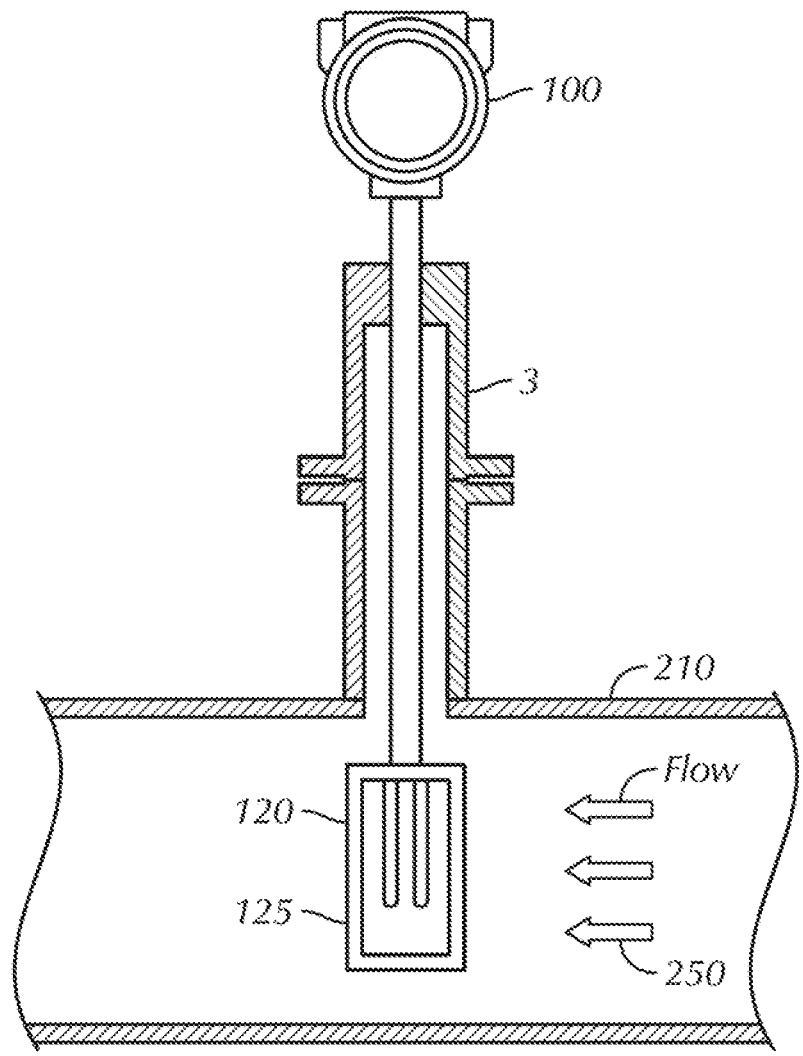
FIG. 2 shows the measurement device installed on a pipeline with the sensor probe exposed to the fluid flowing through the pipeline.

Often measurements of oil water fluid mixtures are made as the fluid is flowing from one location to another through a conduit as illustrated in FIG. 2. Thus, it is important that the fluid flow 250 is in direct contact with both the transmitting antenna 126 and the receiving antenna 128 of the measurement device 100.

One embodiment of the measurement device 100 includes a central processing unit 140 with a microprocessor 102 and an analog to digital converter 142; a transmitter 110 in communication with the microprocessor 102, where the transmitter 110 has a phase locked loop 112 and a voltage controlled oscillator 114; a receiver 130 in communication with the microprocessor 102, where the receiver has a filter 132, an amplifier 134, and a root mean square converter 136; a reference oscillator 150 in communication with the phase locked loop 112; and a sensor probe 120 in communication with the transmitter 110 and the receiver 130, where the sensor probe 120 includes a probe body 122 having a fluid opening 124 for allowing, a fluid mixture to flow through the probe body 122, a transmitting antenna 126 where the transmitting antenna 126 receives a range of microwave frequencies generated by the transmitter 110 and transmits the range of microwave frequencies to the fluid mixture and a receiving antenna 128 that receives the signals of the range of microwave frequencies after being transmitted through the fluid mixture and sends the received microwave frequency signals to the receiver 130. The receiver 130 amplifies each frequency signal received and sends the frequency signals to the central processing unit 140. The analog to digital converter 142 digitizes the amplified frequency signals and the microprocessor 102 identifies the received frequency signal having the lowest amplitude of any of the range of transmitted frequencies. The identified amplitudinal null or nadir is used by the microprocessor 102 to calculate the percentage of water in the fluid mixture.

A spectrum of microwave frequencies is selected for use in determining the water content of the oil water mixture. This preselected spectrum of frequencies, referred to as the frequency sweep or the band of selected frequencies, is generated by the transmitter 110 as described below. The transmitter 110 includes a phase locked loop 112 and a voltage control oscillator 114.

The microprocessor 102 located on the central processing unit 140 communicates bidirectionally with the phase locked loop 112 of the transmitter 110. The microprocessor 102 transmits the requests for specific frequency emissions in the spectrum of preselected frequencies and receives the confirmation or lock of those frequencies from the phase locked loop 112.

The voltage control oscillator 114 generates a series of signals over the preselected spectrum of frequencies (i.e., the frequency sweep). One frequency sweep used for the measurement of components in a fluid mixture is 300 MHz to 300 GHz. Another frequency sweep that is optionally selected for the measurement of water concentration in an oil water fluid mixture is 500 MHz to 1 GHz. The frequencies are generated by variations in the voltage.

The phase locked, loop 112 monitors the frequencies from the voltage control oscillator 114 and receives frequency lock requests from the microprocessor 102. The phase locked loop 112 uses the reference oscillator 150 to confirm the desired frequency and locks specific signals to specific frequencies and confirms the locks to the microprocessor 102.

The transmitter 110 then sends the specific locked frequencies through a coaxial cable 116 to a transmitting antenna 126 positioned within the probe body 122 so that it is in contact with the fluid flow 250. The transmitting antenna 126 transmits the specific locked frequencies in the preselected spectrum of frequencies into the fluid mixture flowing through the conduit or pipeline 210.

The transmitted frequency signals are picked up by the receiving antenna 128 after they have interacted with the fluid mixture. The receiving antenna 128, like the transmitting antenna 126, is positioned within the probe body 122 so that it is in contact with the fluid flow 250. The receiving antenna 128 is connected to a coaxial cable 118. The received frequency signals, after interacting with the fluid mixture, are transmitted from the receiving antenna 128 to the receiver 130.

The receiver 130 has a filter 132, an amplifier 134, a root mean square converter 136, and a resistance thermal device 162. Each of the received frequency signals is transmitted to the receiver 130 where it is passed through the filter 132 in order to filter out the background noise from the desired frequency signal. The filter 132 also blocks unwanted harmonics and acts as an inductor to prevent sparks from penetrating the probe body 122.

The filtered frequency signals is then passed to one or more amplifiers 134 which proportionally amplify the signal strength of the filtered frequency signals. The amplified frequency signals are then transmitted to the root mean square converter 136 which converts the frequency signals into an equivalent voltage signal. The voltage signal is then passed to the analog to digital converter 142 in the central processing unit 140. The analog to digital converter 142 converts the voltage signal to a digital signal.

One advantage of the measurement device is that because it uses the amplitudinal nadir of the received spectrum of signal frequencies to determine water concentration in the fluid mixture and does not measure the power to generate that spectrum of frequencies, the measurement device is able to use a two port system with separated transmitting and receiving electronics. This separation of the transmitting and receiving electronics enables the use of a phase locked loop 112 to generate the specific frequencies in the preselected spectrum. The phase locked loop 112 is quite stable and does not suffer from drifts caused by temperature, aging and so forth; therefore, the measurement device does not require the addition of a reference antenna to compensate for drift.

The microprocessor 102 identifies the frequency signal in the frequency spectrum that has the lowest amplitude after reacting with the fluid mixture. The frequency identified as having the lowest amplitude is used by the microprocessor 102 to determine the water concentration in the fluid mixture.

Since the measurement device itself is subject to very large ambient temperature ranges, from arctic cold to desert heat, maintaining temperature control of the more sensitive electronic components in the transmitter 110 and the receiver 130 will enhance the overall system performance. This is accomplished by using a thermoelectric cooler 170. The thermoelectric cooler 170 is typically attached to the bottom of the printed circuit boards for the transmitter 110 and the receiver 130.

The thermoelectric cooler 170 monitors the temperatures of the boards in both the transmitter 110 and the receiver 130. The board temperatures are digitized by the analog to digital converter 142 and communicated to the central processing unit 140. The microprocessor 102 monitors the temperature of the boards and prevents them from overheating via a feedback path to the thermoelectric cooler 170.

The thermoelectric cooler 170 is capable of heating or cooling. Thus if the temperature exceeds a set point temperature, then thermoelectric cooler 170, under the microprocessor's 102 control, outputs a current such that thermoelectric cooler 170 cools. Likewise, if the temperature drops below the set point temperature, the microprocessor 102 changes the current so that thermoelectric cooler 170 increases its temperature.

The frequency signals received by the receiving antenna are sensitive to changes in the temperature and density of the fluid mixture. The probe sensor includes a temperature sensor for monitoring the temperature of the fluid mixture and an external densitometer 160 measures the density of the fluid mixture. Thus, the microprocessor 102 receives data on the fluid temperature and density and uses that data to compensate for fluid density and temperature changes.

A resistance thermal device 162 monitors the temperature of the fluid flow 250. The temperature measurements are sent to the analog to digital converter 142 and converted to a digital temperature signal. The digital temperature signal is sent to the central processing unit 140 and used by the microprocessor 102 to mathematically compensate for any temperature changes.

Similarly, an external, independent densitometer 160 monitors the density of the oil water mixture. The density measurements are sent to the analog to digital converter 142 and converted to a digital density signal. The digital density signal is sent to the central processing unit 140 and used by the microprocessor 102 to mathematically compensate for any density changes.

Methodology

A plurality of microwave frequencies in a spectrum of frequencies is selected to probe a fluid mixture. One frequency sweep used for the measurement of components in a fluid mixture is 300 MHz to 300 GHz. Another frequency sweep that is optionally selected for the measurement of water concentration in an oil water fluid mixture is 500 MHz to 1 GHz.

The specific frequencies within the spectrum of frequencies are locked by the phase locked loop 112, the voltage control oscillator 114, and the reference oscillator 150. The measurement device transmits each selected frequency from the transmitting antenna 126 into the fluid flow 250 and receives the frequency signal from the fluid flow 250 of the fluid mixture on the receiving, antenna 128.

The fluid mixture is probed with the preselected spectrum of specific frequencies and the frequency signal for each specific frequency is amplified and digitized. When the amplitude of each frequency signal is measured and compared with the other frequencies in the spectrum of frequencies, a clearly identifiable low point or amplitudinal nadir is seen. A plot of the amplitude of the frequency signals provides a generally symmetrical downward projecting peak having a specific low point or amplitudinal nadir as illustrated in FIG. 3A.

Figure 3A:
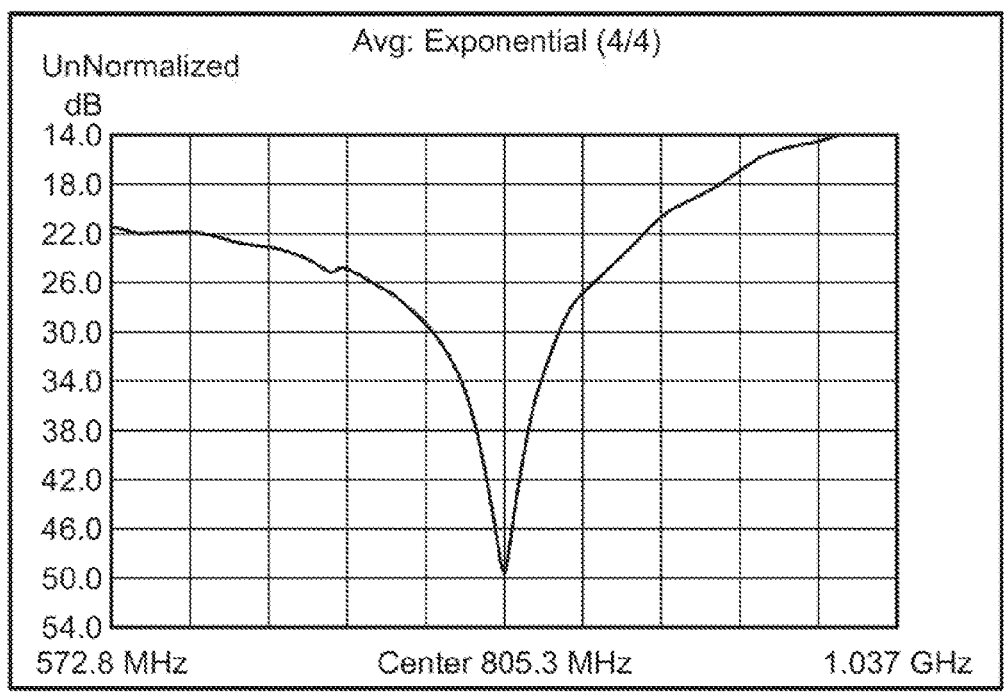
FIGS. 3A and 3B each show a plot of frequency versus signal amplitude of a spectrum of frequencies transmitted through dry hydraulic oil by a transmitting antenna and the frequency signal detected after interaction with the hydraulic oil by a receiving antenna.
Figure 3B:
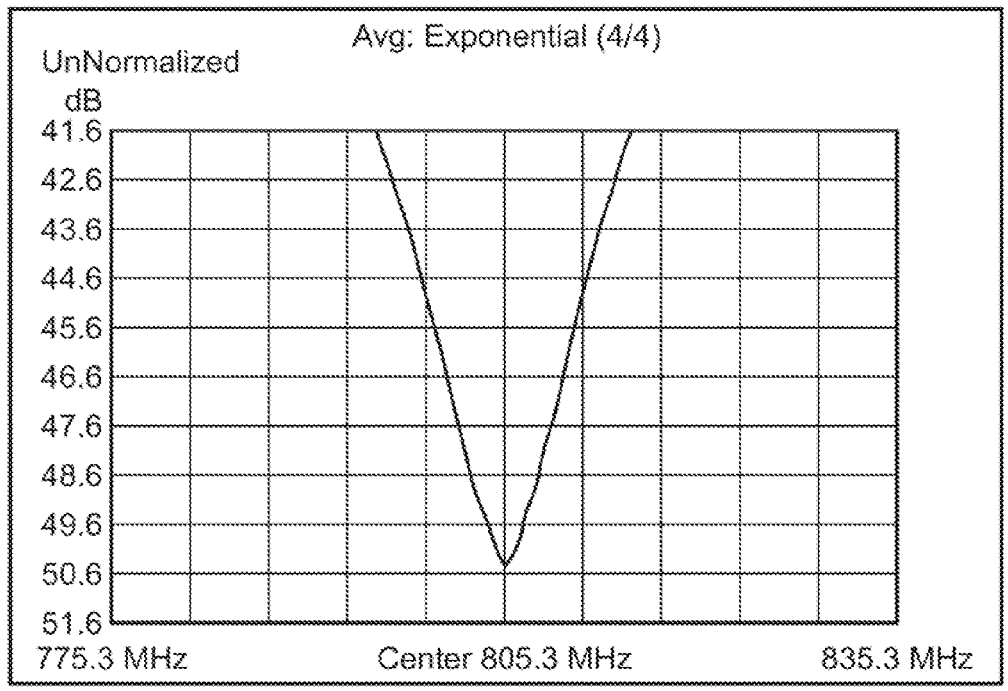

FIGS. 3A and 3B illustrate a plot of the amplitude of the frequency signals for a spectrum of frequencies from about 500 MHz to about 1 GHz that were transmitted and received through a dry hydraulic oil sample. An amplitudinal nadir of 805.3 MHz is clearly identifiable. FIG. 3A plots the signal amplitudes on a vertical axis of 4 db per vertical division for a 465.2 MHz frequency spectrum (i.e., 572.8 MHz to 1.037 GHz). Similarly, FIG. 3B plots the signal amplitudes on a vertical axis of 1 db per vertical division for a 60 MHz frequency spectrum (i.e., 775.3 MHz to 835.3 MHz).

Figure 4:
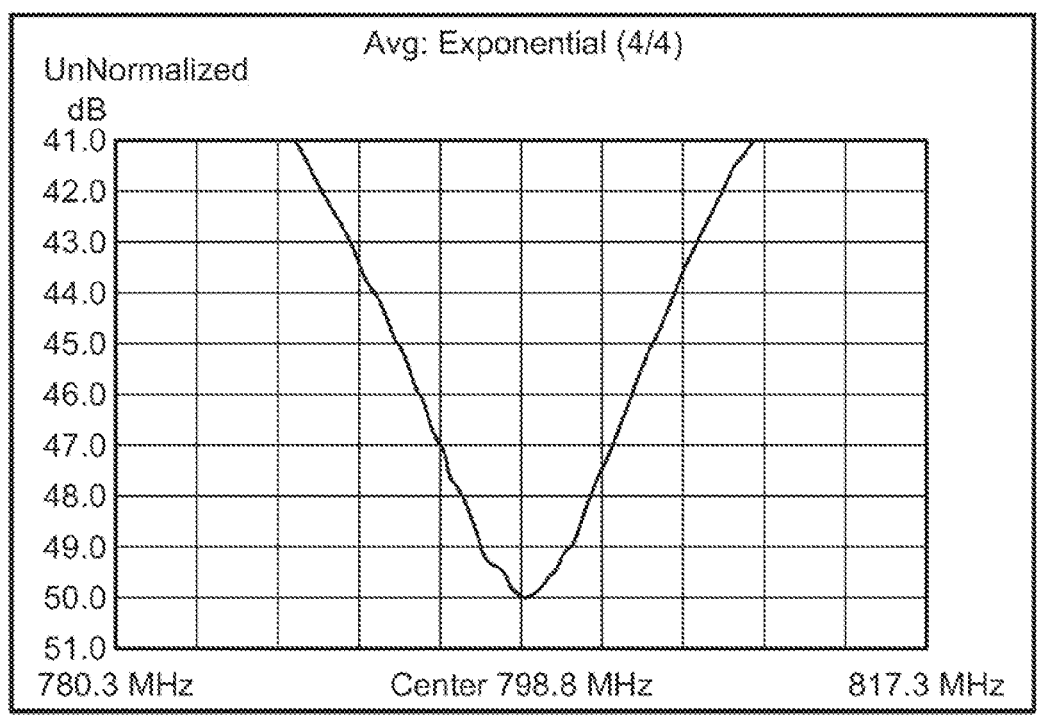
FIG. 4 is a plot of frequency versus signal amplitude of a spectrum of frequencies transmitted through hydraulic oil containing 0.57% water by the transmitting antenna and the frequency signal detected by the receiving antenna from the hydraulic oil water mixture.

As water is added to the hydraulic oil sample the frequency of the amplitudinal nadir shifts. For example, when 0.57% water was added to the hydraulic oil and the amplitudes of the frequency signals for a spectrum of frequencies from 794.8 MHz to 814.8 MHz were plotted the amplitudinal nadir was shifted by 6.5 MHz to 798.8 MHz as shown in FIG. 4.

The shift in the amplitudinal nadir of the amplitude plots that occurs when various percentages of water were added to the oil water mixture was plotted. Plotting multiple known nadir frequency shifts for varying water percentages in a given fluid mixture creates a plot representing the nadir frequency shift for any given percentage of water in a similar fluid mixture.

Figure 5:
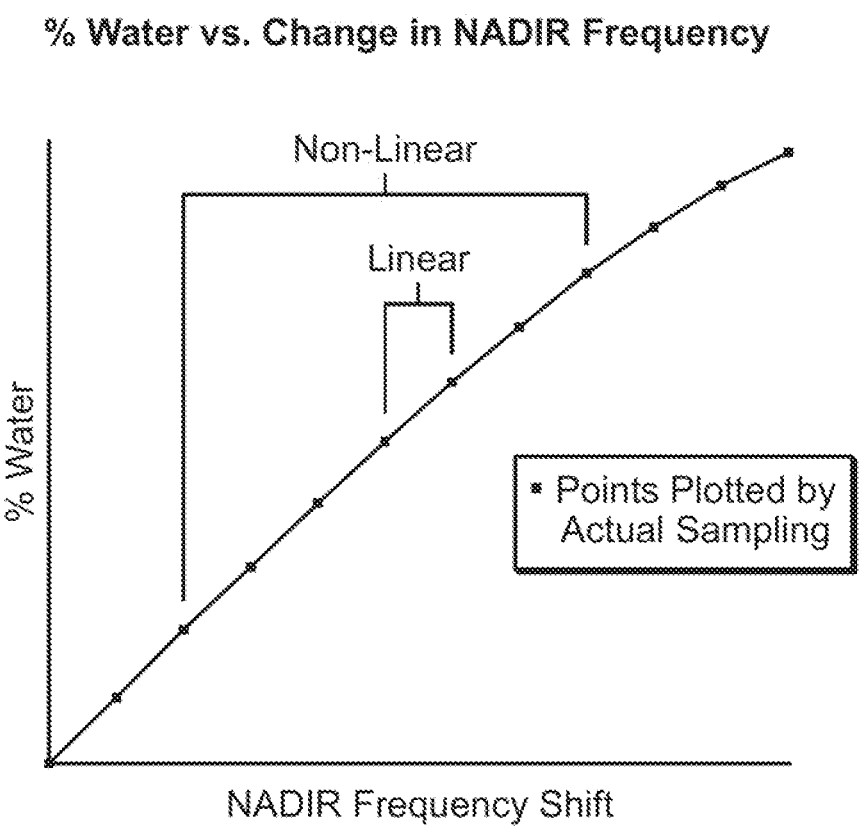
FIG. 5 is a schematic representation of a plot of shifts in the amplitudinal null or amplitudinal nadir frequency versus the percentage of water in the fluid mixture.

As seen in FIG. 5, the plot of nadir frequency shifts with increasing, water concentrations in a fluid, mixture gives a somewhat non-linear plot over a relatively large variation in the percentage of water in a fluid mixture. However, as the nadir frequency shifts are plotted for smaller and smaller increments in water concentration in the fluid mixture the plot approaches linearity as seen in FIG. 5. Thus, a nadir frequency shift plot of a fluid mixture having very small increments in the water concentration added to the fluid mixture is utilized to create a linear like plot, that can be used to determine the water concentration in fluid mixtures having a water concentration falling within the range of the water concentration of the plotted samples.

Although the measurement device can measure a variety of water concentrations in oil, a preferred embodiment of the measurement device is designed to determine the exact water concentration in an oil water mixture when the concentration of writer equals about 5% or less of the oil water mixture.

It has been noted that the nadir frequency shift can vary slightly with changes in the density or the temperature of the fluid mixture. The measurement device includes an input means for density measurements from an external densitometer 160 and from an internal resistance thermal device 162. Thus, the measurement device can be calibrated for the specific density and temperature of the fluid mixture.

Although the present invention and its advantages have been described in detail, it should be understood that various changes, substitutions and alterations can be made herein without departing from the spirit and scope of the invention as defined by the appended claims.

What is claimed is:

1. A device for determining the concentration of fluid components within a fluid mixture comprising:
 a) a microprocessor;
 b) a transmitter in communication with the microprocessor, the transmitter having a phase locked loop and a voltage controlled oscillator, wherein the transmitter generates and transmits a range of microwave frequencies;
 c) a receiver in communication with the microprocessor;
 d) a reference oscillator in communication with the phase locked loop of the transmitter; and
 e) a sensor probe including:
  (i) a first transmitting antenna in communication with the transmitter, wherein the transmitting antenna receives the range of microwave frequencies generated by the transmitter and transmits the range of microwave frequencies to a fluid mixture,
  (ii) a second receiving antenna positioned proximal the first transmitting antenna, wherein the second receiving antenna is in communication with the receiver, the receiving antenna receives a signal from each frequency in the range of microwave frequencies transmitted through the fluid mixture by the transmitting antenna, and (iii) a probe body having a fluid opening for allowing the fluid mixture to flow through the probe body in communication with the transmitting antenna and the receiving antenna;

whereby the received frequency signal of each transmitted frequency of the range of microwave frequencies is communicated to the microprocessor via the receiver and is used to calculate a percentage of water in the fluid mixture based on an identified transmitted frequency that results in a minimal received frequency signal after reacting with the fluid mixture.

2. The device of claim 1, wherein the receiver includes a filter, an amplifier, and a root mean square converter.

3. The device of claim 1, further including an analog to digital converter.

4. The device of claim 1, further including a temperature sensor in communication with the fluid mixture.

5. The device of claim 4, wherein the temperature sensor communicates the temperature of the fluid mixture to the receiver.

6. The device of claim 1, wherein the phase locked loop communicates with the reference oscillator, the microcontroller and the voltage controlled oscillator to lock each frequency in the range of microwave frequencies transmitted by the transmitter to the transmitting antenna.

7. The device of claim 1, further including a thermoelectric cooler for maintaining the transmitter and the receiver at a preselected temperature.

8. The device of claim 1, wherein a densitometer communicates a density of the fluid mixture to the microprocessor.

9. A device for determining the concentration of water within a fluid mixture comprising:
   a) a central processing unit having a microprocessor and an analog to digital converter;
   b) a transmitter in communication with the microprocessor, the transmitter having a phase locked loop and a voltage controlled oscillator, wherein the transmitter generates and transmits a range of microwave frequencies comprising a plurality of locked frequencies;
   c) a receiver having a filter, an amplifier, and a root mean square converter, the receiver in communication with the analog to digital converter;
   d) a reference oscillator in communication with the phase locked loop; and
   c) a sensor probe including:
      (i) a first transmitting antenna in communication with the transmitter, wherein the transmitting antenna receives the range of microwave frequencies generated by the transmitter and transmits the range of microwave frequencies to a fluid mixture,
      (ii) a second receiving antenna positioned proximal the first transmitting antenna, wherein the second receiving antenna is in communication with the receiver, the receiving antenna receives a signal from each locked frequency in the range of microwave frequencies transmitted through the fluid mixture by the transmitting antenna and wherein each received frequency signal of the range of microwave frequencies received from the fluid mixture by the receiving antenna is digitized by the analog to digital converter and used by the microprocessor to identify the transmitted frequency resulting in an amplitudinal nadir of the plurality of received frequency signals to thereby calculate a percentage of water in the fluid mixture, and
      (iii) a probe body having a fluid opening for allowing the fluid mixture to flow through the probe body in communication with the transmitting antenna and the receiving antenna.

10. The device of claim 9, wherein the phase locked loop communicates with the reference oscillator, the microcontroller and the voltage controlled oscillator to lock each frequency in the range of microwave frequencies transmitted by the transmitter to the transmitting antenna.

11. The device of claim 9, further including a thermoelectric cooler for maintaining the transmitter and the receiver at a preselected temperature.

12. A method for detecting the percentage of water in a fluid mixture including the steps of:
   (a) positioning a sensor probe of a measurement device within a fluid mixture, wherein the measurement device includes:
      (i) a microprocessor,
      (ii) a transmitter having a phase locked loop and a voltage controlled oscillator, the transmitter in communication with the microprocessor,
      (iii) a receiver in communication with the microprocessor,
      (iv) a reference oscillator in communication with the phase locked loop, and
      (v) a sensor probe having a first transmitting antenna in communication with the transmitter and a second receiving antenna proximal the first transmitting antenna that is in constant communication with the receiver, and a probe body having a fluid opening for allowing the fluid mixture to flow through the probe body in communication with the transmitting antenna and the receiving antenna;
   (b) selecting a spectrum of microwave frequencies, wherein the spectrum includes a plurality of frequencies;
   (c) utilizing the phase locked loop and the reference oscillator to lock a request for each of the plurality of frequencies into the voltage controlled oscillator;
   (d) generating each of the locked frequencies in the spectrum;
   (e) transmitting the generated locked frequencies to the fluid mixture via the transmitting antenna;
   (f) receiving a signal via the receiving antenna from each of the transmitted frequencies after each frequency has interacted with the fluid mixture;
   (g) identifying a specific frequency within the spectrum of frequencies having a lowest amplitude of the received frequency signals; and
   (h) computing a percentage of water in the fluid mixture based on the specific frequency with the lowest amplitude in the received spectrum of frequency signals.

13. The method of claim 12, wherein the fluid mixture is an oil water mixture.

14. The method of claim 12, wherein the percentage of water within the fluid mixture is equal to 5% or less of the fluid mixture.

15. The method of claim 12, further comprising the steps of measuring a temperature and a density of the fluid mixture and mathematically compensating for the fluid temperature and density in the computation of the percentage of water.

16. A method for detecting the percentage of water in a fluid mixture including the steps of:
   (a) positioning a sensor probe of a measurement device within a fluid mixture, wherein the measurement device includes:
      (i) a microprocessor and an analog to digital converter, (ii) a transmitter having a phase locked loop and a voltage controlled oscillator, the transmitter in communication with the microprocessor, (iii) a receiver having a filter, an amplifier, and a root mean square converter, the receiver in communication with the microprocessor, (iv) a reference oscillator in communication with the phase locked loop, and (v) a sensor probe having a first transmitting antenna in communication with the transmitter, a second receiving antenna proximal the first transmitting antenna that is in communication with the receiver, and a probe body having a fluid opening for allowing the fluid mixture to flow through the probe body in communication with the transmitting antenna and the receiving antenna;

(b) selecting a spectrum of microwave frequencies, wherein the spectrum includes a plurality of frequencies;

(c) utilizing the phase locked loop and the reference oscillator to lock a request for each of the plurality of frequencies into the voltage controlled oscillator;

(d) generating each of the locked frequencies;

(e) transmitting the generated frequencies to the fluid mixture via the transmitting antenna;

(f) receiving a signal via the receiving antenna from each of the transmitted locked frequencies after each frequency has interacted with the fluid mixture;

(g) filtering each received frequency signal;

(h) amplifying each received frequency signal;

(i) digitizing each received frequency signal;

(j) transmitting each digitized received frequency signal to the microprocessor, wherein the microprocessor identifies a specific frequency within the spectrum of frequencies having a lowest amplitude of the received frequency signals; and (k) computing a percentage of water in the fluid mixture based on the specific frequency with the lowest amplitude in the received spectrum of frequency signals.

17. The method of claim 16, wherein the fluid mixture is an oil water mixture containing water at a concentration of 5% or less.

18. The method of claim 16, wherein the computation of the percentage of water includes a compensation for the fluid temperature.

19. The method of claim 16, wherein the computation of the percentage of water includes a compensation for the fluid density.

20. The method of claim 16, further comprising the step of maintaining the transmitter and the receiver at a preselected range of temperatures.

* * * * *